(12) United States Patent
Rozenberg et al.

(10) Patent No.: US 8,308,786 B2
(45) Date of Patent: Nov. 13, 2012

(54) METHODS AND DEVICES FOR NON-INVASIVE CEREBRAL AND SYSTEMIC COOLING VIA THE NASAL CAVITY

(75) Inventors: Allan Rozenberg, Poway, CA (US); Denise Barbut, New York, NY (US); John K. Hoffman, Poway, CA (US)

(73) Assignee: BeneChill, Inc., San Diego, CA (US)

( * ) Notice: Subject to any disclaimer, the term of this patent is extended or adjusted under 35 U.S.C. 154(b) by 946 days.

(21) Appl. No.: 12/038,720

(22) Filed: Feb. 27, 2008

(65) Prior Publication Data
US 2008/0215002 A1 Sep. 4, 2008

Related U.S. Application Data

(60) Provisional application No. 60/903,931, filed on Feb. 28, 2007.

(51) Int. Cl.
| | |
|---|---|
| *A61F 7/12* | (2006.01) |
| *A61F 7/00* | (2006.01) |
| *A61B 18/00* | (2006.01) |
| *A61M 25/00* | (2006.01) |
| *A61M 31/00* | (2006.01) |

(52) U.S. Cl. ......... 607/105; 607/96; 607/104; 607/113; 604/254; 604/514

(58) Field of Classification Search ............ 607/105, 607/96, 104, 113; 604/514, 113
See application file for complete search history.

(56) References Cited

U.S. PATENT DOCUMENTS

| | | | |
|---|---|---|---|
| 5,492,538 A * | 2/1996 | Johlin, Jr. | 604/264 |
| 6,090,132 A | 7/2000 | Fox | |
| 6,156,057 A | 12/2000 | Fox | |
| 6,736,837 B2 | 5/2004 | Fox | |
| 2005/0209662 A1* | 9/2005 | Lunderqvist et al. | 607/105 |

* cited by examiner

*Primary Examiner* — Roy Gibson
*Assistant Examiner* — Jared W Pike
(74) *Attorney, Agent, or Firm* — O'Melveny & Myers LLP

(57) ABSTRACT

A method for cerebral and systemic cooling by circulating a cold liquid through a nasal catheter looped through the patient's nasal cavities and around the nasal septum. The nasal catheter is inserted into the patient's first nostril, advanced through the nasal cavity, around the nasal septum and out of the patient's second nostril. A cold fluid having a temperature between about −20° C. and about 37° C. is flowed though a lumen in the nasal catheter to cool the nasal cavity. The nasal catheter may have one or more flexible balloons mounted on the catheter such that when the catheter is looped around the nasal septum, the balloon(s) are positioned in a portion of the patient's first and second nasal cavities. When a cold liquid is circulated through the catheter lumen, the flexible balloons expand to a contact the inner walls of the nasal cavities and provide direct cooling of the nasal cavities.

21 Claims, 10 Drawing Sheets

METHODS AND DEVICES FOR NON-INVASIVE CEREBRAL AND SYSTEMIC COOLING VIA THE NASAL CAVITY

This patent claims the benefit of the U.S. provisional patent application Ser. No. 60/903,931, entitled "Pull-Through Balloon for Nasal Cooling," filed Feb. 28, 2007 which is expressly incorporated herein by reference in its entirety for all purposes.

FIELD OF THE INVENTION

The invention relates to cerebral and systemic cooling via the nasal cavity and more particularly to methods and devices for using a nasal catheter to deliver liquids the nasopharyngeal cavity for cerebral and systemic cooling.

BACKGROUND OF THE INVENTION

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal. Global cerebral ischemia refers to reduction of blood flow within the cerebral vasculature resulting from systemic circulatory failure caused by, e.g., shock, cardiac failure, or cardiac arrest. Within minutes of circulatory failure, tissues become ischemic, particularly in the heart and brain.

The most common form of shock is cardiogenic shock, which results from severe depression of cardiac performance. The most frequent cause of cardiogenic shock is myocardial infarction with loss of substantial muscle mass. Pump failure can also result from acute myocarditis or from depression of myocardial contractility following cardiac arrest or prolonged cardiopulmonary bypass. Mechanical abnormalities, such as severe valvular stenosis, massive aortic or mitral regurgitation, acutely acquired ventricular septal defects, can also cause cardiogenic shock by reducing cardiac output. Additional causes of cardiogenic shock include cardiac arrhythmia, such as ventricular fibrillation. With sudden cessation of blood flow to the brain, complete loss of consciousness is a sine qua non in cardiac arrest. Cardiac arrest often progresses to death within minutes if active interventions, e.g., cardiopulmonary resuscitation (CPR), defibrillation, use of inotropic agents and vasoconstrictors such as dopamine, dobutamine, or epinephrine, are not undertaken promptly. The most common cause of death during hospitalization after resuscitated cardiac arrests is related to the severity of ischemic injury to the central nervous system, e.g., anoxic encephalopathy. The ability to resuscitate patients of cardiac arrest is related to the time from onset to institution of resuscitative efforts, the mechanism, and the clinical status of the patient prior to the arrest.

Focal cerebral ischemia refers to cessation or reduction of blood flow within the cerebral vasculature resulting in stroke, a syndrome characterized by the acute onset of a neurological deficit that persists for at least 24 hours, reflecting focal involvement of the central nervous system. Approximately 80% of the stroke population is hemispheric ischemic strokes, caused by occluded vessels that deprive the brain of oxygen-carrying blood. Ischemic strokes are often caused by emboli or pieces of thrombotic tissue that have dislodged from other body sites or from the cerebral vessels themselves to occlude in the narrow cerebral arteries more distally. Hemorrhagic stroke accounts for the remaining 20% of the annual stroke population. Hemorrhagic stroke often occurs due to rupture of an aneurysm or arteriovenous malformation bleeding into the brain tissue, resulting in cerebral infarction. Other causes of focal cerebral ischemia include vasospasm due to subarachnoid hemorrhage from head trauma or iatrogenic intervention.

Current treatment for acute stroke and head injury is mainly supportive. A thrombolytic agent, e.g., tissue plasminogen activator (t-PA), can be administered to non-hemorrhagic stroke patients. Treatment with systemic t-PA is associated with increased risk of intracerebral hemorrhage and other hemorrhagic complications. Aside from the administration of thrombolytic agents and heparin, there are no therapeutic options currently on the market for patients suffering from occlusion focal cerebral ischemia. Vasospasm may be partially responsive to vasodilating agents. The newly developing field of neurovascular surgery, which involves placing minimally invasive devices within the carotid arteries to physically remove the offending lesion, may provide a therapeutic option for these patients in the future, although this kind of manipulation may lead to vasospasm itself.

In both stroke and cardiogenic shock, patients develop neurological deficits due to reduction in cerebral blood flow. Thus treatments should include measures to maintain viability of neural tissue, thereby increasing the length of time available for interventional treatment and minimizing brain damage while waiting for resolution of the ischemia. New devices and methods are thus needed to minimize neurologic deficits in treating patients with either stroke or cardiogenic shock caused by reduced cerebral perfusion.

Research has shown that cooling the brain may prevent the damage caused by reduced cerebral perfusion. Initially research focused on selective cerebral cooling via external cooling methods. Studies have also been performed that suggest that the cooling of the upper airway can directly influence human brain temperature, see for example *Direct cooling of the human brain by heat loss from the upper respiratory tract*, Zenon Mariak, et al. 8750-7587 *The American Physiological Society* 1999, incorporated by reference herein in its entirety. Furthermore, because the distance between the roof of the nose and the floor of the anterior cranial fossa is usually only a fraction of a millimeter, the nasal cavity might be a site where respiratory evaporative heat loss or convection can significantly affect adjacent brain temperatures, especially because most of the warming of inhaled air occurs in the uppermost segment of the airways. Thus, it would be advantageous to develop a device and method for achieving cerebral cooling via the nasal cavity of a patient.

SUMMARY OF THE INVENTION

The invention relates to methods and devices for cerebral cooling via the nasal cavity. The cooling occurs by direct heat transfer through the nasopharynx as well as by hematogenous cooling through the carotids as they pass by the oropharynx and through the Circle of Willis, which lies millimeters away from the pharynx. The direct cooling will be obtained through heat loss of a cooled liquid in the nasal cavity. Additionally, cooling may occur through convection in the nasal cavity. Such cerebral cooling may help to minimize neurologic deficits in treating patients with either stroke or cardiogenic shock caused by reduced cerebral perfusion or in the treatment of migraines. Among the many important advantages of the present invention is patient safety by comparison with transpulmonary and intravascular cooling methods and devices.

In one embodiment, the invention provides a method for cerebral cooling. An elongate tubular member can be inserted into a nasal cavity of a patient through one of the patient's nostrils. The elongate tubular member may have a proximal end, a distal end, a lumen extending therebetween and an expandable region intermediate between the distal and proximal ends. The distal end of the elongate tubular member may be advanced through the patient's nasal cavity, around the nasal septum and out of the patient's other nostril such that the expandable region is positioned within the patient's nasal cavity. A cold liquid, such as cooled saline, a perfluorocarbon or any other suitable cold liquid may be circulated through the lumen at the proximal end of the elongate tubular member, through the expandable region and through the lumen at the distal end of the catheter to cool the nasal cavity. The circulation of cooled liquid through the nasal cavity results in reduction of the cerebral temperature of the patient by at least 0.1° C. in one hour. Alternatively, the cerebral temperature may be reduced by at least 1° C. in one hour, alternatively at least 2° C., alternatively at least 3° C., alternatively at least 4° C., alternatively at least 5° C., alternatively at least 6° C., alternatively at least 7° C., alternatively at least 8° C., alternatively at least 9° C., alternatively at least 10° C.

The method may further include the step of recirculating the liquid by infusing the liquid through the proximal end of the lumen of the elongate tubular member and withdrawing the liquid through the distal end of the lumen of the elongate tubular member. The liquid may be infused using a pump at a flow rate of between about 5 ml/min and about 5 L/min, alternatively between about 100 ml/min and about 1 L/min, alternatively between about 200 ml/min and about 800 ml/min, alternatively between about 300 ml/min and about 700 ml/min, alternatively between about 400 ml/min and about 600 ml/min, alternatively between about 450 ml/min and about 550 ml/min, alternatively about 500 ml/min.

In some embodiments, the elongate tubular member may be positioned within the patient's nasal cavity by advancing the distal end of the elongate tubular member through the patient's first nostril to a point past the septum. A grasping tool may then be advanced through the patient's second nostril to a point past the nasal septum. The grasping tool may grasp, or otherwise engage, the distal end of the elongate tubular member such that withdrawing the grasping tool from the patient's second nostril will pull the distal end of the elongate tubular member around the nasal septum and out of the patient's second nostril.

In an alternative embodiment, the invention provides a cooling assembly for insertion into a patient's nasal cavity through the patient's nostrils. The cooling assembly includes catheter having a proximal end, a distal end, a lumen therebetween and a first balloon mounted on the catheter at a location intermediate between the proximal and distal ends. A magnet is located on the distal end of the catheter. The catheter is adapted for the distal end to be advanced through the patient's first nostril, around the nasal septum and out of the second nostril to position the first balloon in a portion of the nasal cavity. An elongate member having distal and proximal ends and a second magnet located on the distal end is configured to be advanced through the patient's second nostril. The second magnet on the distal end of the elongate member is configured to engage the first magnet on the distal end of the catheter to magnetically couple the distal end of the catheter and the distal end of the elongate member such that in use, when the elongate member is withdrawn from the patient's second nostril, the distal end of the catheter will be pulled around the nasal septum and out of the patient's second nostril. The first balloon is mounted on the catheter such that it will be positioned within the nasal cavity once the distal end of the catheter has been pulled through the second nostril. The first balloon is configured such that in use, when a cold fluid is circulated through the lumen of the catheter and the balloon, the balloon will expand to fill at least a portion of the nasal cavity to cool the nasal cavity. In some embodiments, a drug may also be eluted from a surface of the balloon.

The cooling assembly may further comprise a second balloon mounted on the catheter at a position intermediate between the proximal and distal ends of the catheter such that when the distal end of the catheter has been pulled through the second nostril, the fist balloon will lie substantially within the patient's first nasal cavity and the second balloon will lie substantially within the patient's second nasal cavity. The second balloon is configured such that in use, when a cold fluid is circulated through the lumen of the catheter and the balloon, the balloon will expand to fill at least a portion of the nasal cavity to cool the nasal cavity.

In use, the distal end of the catheter is advanced through the patient's first nostril to a point beyond the nasal septum. The elongate member is then advanced through the patient's second nostril to appoint beyond the nasal septum such that the magnet on the distal end of the elongate tubular member engages the magnet on the distal end of the catheter and magnetically couples the distal end of the catheter to the distal end of the elongate member. The elongate member is then withdrawn from the patient's second nostril pulling the distal end of the catheter around the nasal septum and out of the patient's second nostril. A cold fluid is circulated through the catheter to expand the one or more balloons such that the one or more balloons expand to substantially fill a portion of the patient's nasal cavities. The cold fluid is introduced or infused through an opening in the lumen at the proximal end of the catheter, circulated through the lumen of the catheter and the balloon(s) and withdrawn, suctioned or drained off from an opening in the lumen at the distal end of the catheter. The cold liquid preferably has a temperature between about −20° C. and about 37° C. For example, the liquid may be, but is not limited to, saline, PFC, or a refrigerant (such as R-134a refrigerant (1,1,1,2 tetrafluoro ethane)). During this process, the one or more balloons expand to place the balloon(s) in contact with portions of the nasal cavities and the nasopharynx.

The method may further include the step of recirculating the liquid by infusing the liquid through the proximal end of the lumen and through the one or more balloons and withdrawing the liquid through the distal end of the lumen. In some embodiments, a fluid reservoir and a pump may be used to continuously circulate cooled liquid through the lumen of the catheter and the balloon(s). For example, the liquid may be infused using a pump at a flow rate of between about 5 ml/min and about 5 L/min, alternatively between about 100 ml/min and about 1 L/min, alternatively between about 200 ml/min and about 800 ml/min, alternatively between about 300 ml/min and about 700 ml/min, alternatively between about 400 ml/min and about 600 ml/min, alternatively between about 450 ml/min and about 550 ml/min, alternatively about 500 ml/min.

DETAILED DESCRIPTION

Figure 1A:
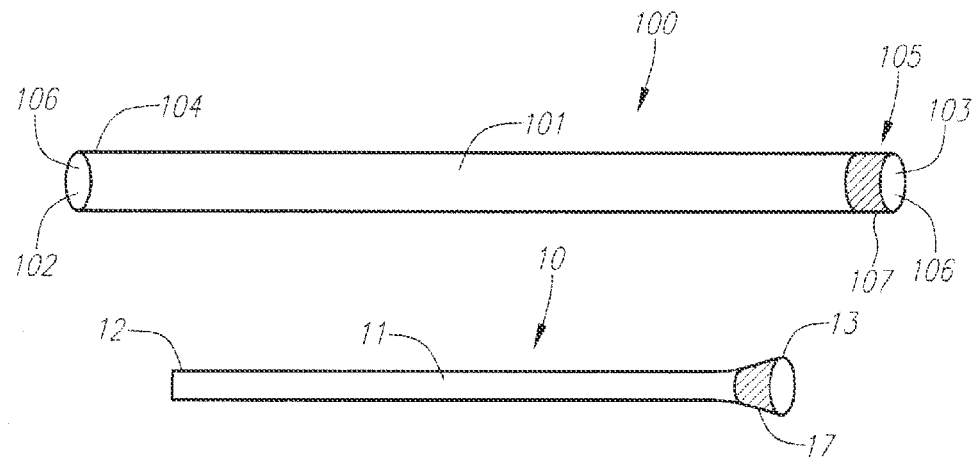
FIG. 1 illustrates an embodiment of a nasal catheter for delivering a cooled liquid to the nasopharyngeal cavity and a grasping tool for pulling the catheter through the nasal cavity according to the present invention for non-invasive cerebral and systemic cooling.
FIG. 1B illustrates a cross-sectional view of an embodiment of the magnet at the distal end of the nasal catheter.
FIG. 1C illustrates a cross-sectional view of an alternative embodiment of the magnet at the distal end of the nasal catheter.

FIG. 1A illustrates a nasal catheter 100 for non-invasive cerebral and systemic cooling of the nasal cavity. Nasal catheter 100 comprises a flexible tubular member 101 with openings 102, 103 at each end 104, 105 of the tubular member 101 and a lumen 106 extending between the openings 102, 103. The flexible tubular member 101 has a length sufficient for extending through a patient's first nostril, around the nasal septum and out the patients second nostril such that the ends 104, 105 of the tubular member extend beyond the patient's nostrils. In some embodiments, the flexible tubular member can have a length such that the first and second ends 104,105 extend substantially beyond the patient's nostrils to allow for attaching the ends 104, 105 to a fluid reservoir and/or a pump for circulating a cold liquid through the lumen 106. The nasal catheter 100 is sufficiently flexible along at least a portion of the flexible tubular member 101 such that it can bend about 180 degrees to navigate around the nasal septum. In some embodiments, the flexible tubular member 101 can have regions of varying flexibility such that the nasal catheter 100 is sufficiently flexible to be navigable around the nasal septum and out of the patient's second nostril while being sufficiently rigid to be easily advanced through the patient's first nostril. It is also important that the flexible tubular member 101 not "kink" or bend so sharply that the lumen 106 constricts such that it is no longer functional.

Figure 1B:
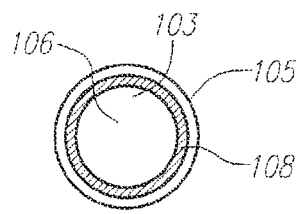
Figure 1C:
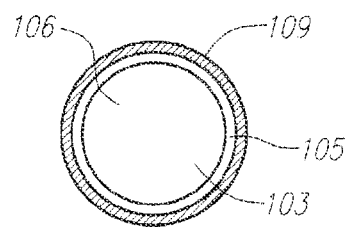

A magnet 107 is located at the distal end 105 of the flexible tubular member 101. The magnet 107 is preferably a rare earth magnet or electromagnet having sufficient magnetic power and strength to attract and couple with another source of magnetic attraction such as a second catheter having a magnet of the opposite polarity. The magnet 107 may be integral to the tubular wall of the distal end 105 of the flexible tubular member 101. Alternatively, the magnet 107 may comprise one or more magnets contained within a separate tubular body attached to the distal end of the flexible tubular member. For example, as shown in FIG. 1B, the magnet 107 may comprise one or more magnets contained within a separate tubular body 108 mounted inside the distal end 105 of the flexible tubular member 101. The tubular body 108 has an outer diameter substantially equal to the inner diameter of the flexible tubular member 101 and an inner diameter sufficient to maintain the opening 103 for lumen 106 at the distal end of the flexible tubular member 101. The tubular body 108 can be secured in the opening 103 at distal end of the flexible tubular member 101 via a friction fit or with an adhesive layer or polymer coating. In an alternative embodiment, as shown in FIG. 1C, the magnet 107 may comprise one or more magnets contained within the tubular wall of a separate tubular body 109 mounted around the outside of the distal end 105 of the flexible tubular member 101. Here, the tubular body 109 has an inner diameter substantially equal to the outer diameter of the distal end of the flexible tubular member 101. The tubular body 109 can be secured over the distal end 105 of flexible tubular member 101, adjacent the opening 103, with an adhesive layer or polymer coating 42, which also provides a smooth transition between the flexible tubular member 101 and the tubular member 109 to provide for smooth passage of the distal end of the catheter 100 through the nasal cavity. In an alternative embodiment, the magnet 107 may be friction fit within the opening 103 at the distal end 105 of the flexible tubular member 101 to attach the magnet to the catheter for placement of the catheter within a patient's nasal cavity. Once the catheter has been pulled though the patient's nasal cavity and out of the patient's second nostril, the distal tip of the flexible tubular member 101 housing the magnet 107 may be cut off to create an opening for lumen 106 in the distal end 105 of the catheter.

Figure 4A:
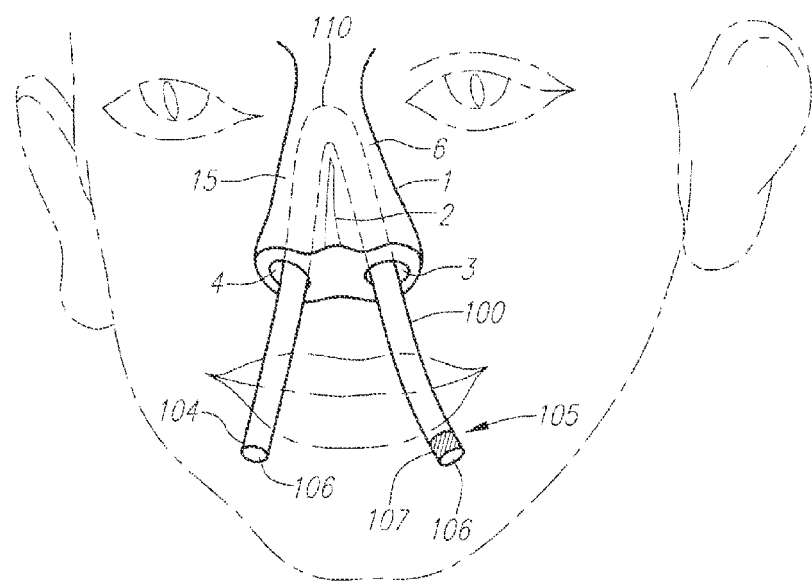
FIG. 4A illustrates the nasal catheter of FIG. 1 positioned in a patient's nasal cavity for circulating a cooled liquid in the nasopharyngeal cavity according to the present invention.
Figure 4B:
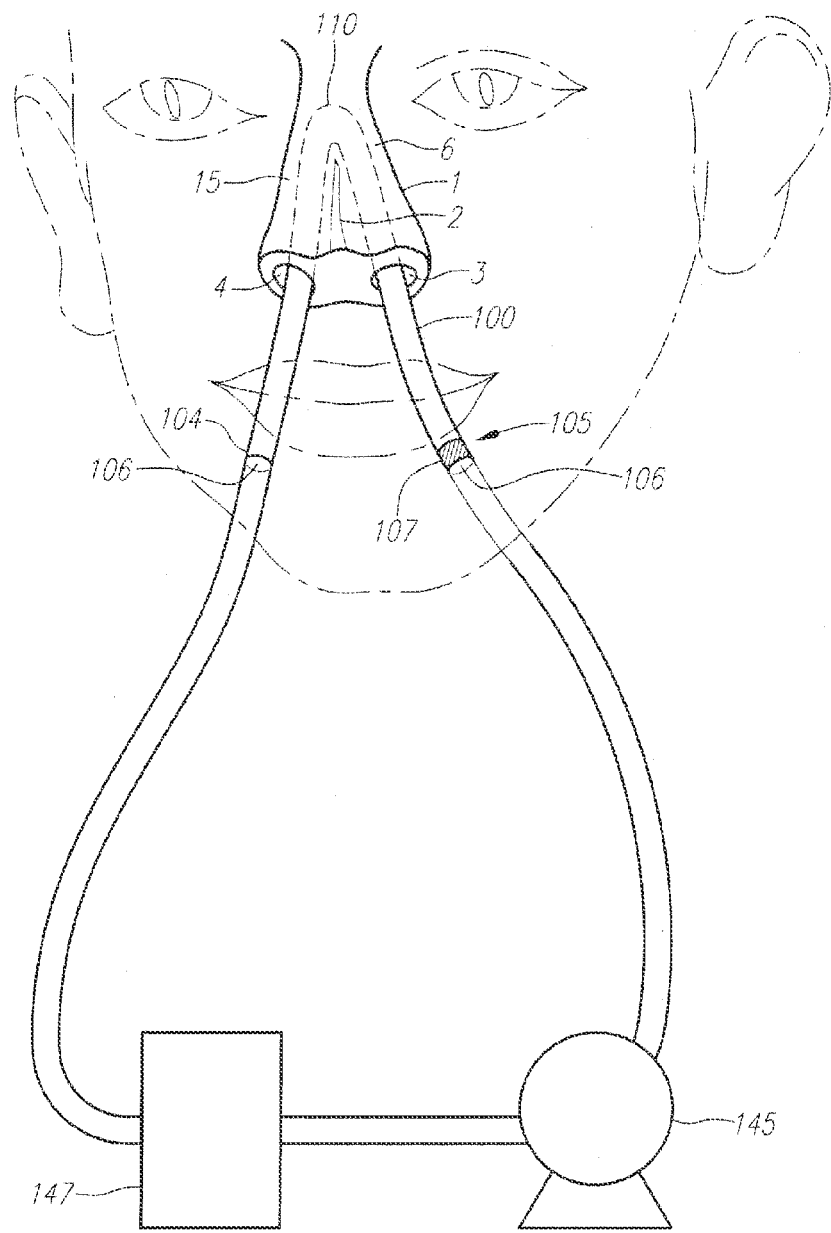
FIG. 4B illustrates an alternative embodiment of the nasal catheter of FIG. 1 positioned in a patient's nasal cavity, including a reservoir and pump, tbr circulating a cooled liquid in the nasopharyngeal cavity according to the present invention.

A central lumen 106 extends between the distal and proximal ends 104, 105 of the flexible tubular member 101 with openings 102, 103 at each end such that a fluid may be circulated through the lumen 106 by introducing the fluid in the first opening 102 at the proximal end 104 of the catheter 100 and withdrawing, suctioning or otherwise removing the fluid at the second opening 103 and the distal end 105 of the catheter 100. In use, as shown in FIGS. 4A and 4B, the catheter 100 can be positioned in the patient's first nostril 4, around the nasal septum 2 and out of the patient's second nostril 3 such that the fluid will flow freely into a first nostril 4, through the patient's nasal cavities 5,6 and out of the second nostril 3. It is no longer necessary to infuse and remove the liquid from a single nostril, for example with a second lumen, therefore the lumen 106 of the catheter 100 can have a much larger diameter. For example, in some embodiments, the central lumen may have a diameter 10 F, alternatively 12 F, alternatively 14 F, alternatively 16 F, alternatively 18 F, alternatively 20 F. The wide, central lumen allows fluid, such as a cold liquid to flow through the catheter as a quicker rate, potentially providing a greater cooling capacity. Additionally, because the cold liquid flows through the catheter, delivery of the cooled liquid to the nasal cavity does not need to be interrupted to suction the used liquid from the catheter.

In some embodiments, the flexible tubular member 101 can have an expandable region located intermediate between the distal and proximal ends of the flexible tubular member 101 such that when a liquid is circulated through the lumen 106, the liquid will cause the cross-sectional diameter of the expandable region to increase. For example, the catheter may comprise a continuous tube with one or more expandable regions between the proximal and distal ends of the catheter. Alternatively, the catheter may be made of contiguous tubular segments wherein the expandable region is made of different tubular materials having different physical properties. In use, as shown in FIG. 4A and 4B, the nasal catheter 100 may be positioned in a patient's nasal cavities 5,6 such that the expandable region 110 is located in the rear portions of the patient's right and left nasal cavities 5,6 and around the nasal septum 2. When a cold liquid is circulated through the nasal catheter 100, the expandable region 110 of the flexible tubular member may expand to substantially fill a portion of the left and right nasal cavities 5,6 and the nasopharynx and touch the adjacent structures to provide increased surface area, increased direct contact area between the flexible tubular member 101 and adjacent structures, and an increase volume of fluid in the nasal cavity to thereby provide an increased cooling capacity.

Figure 2A:
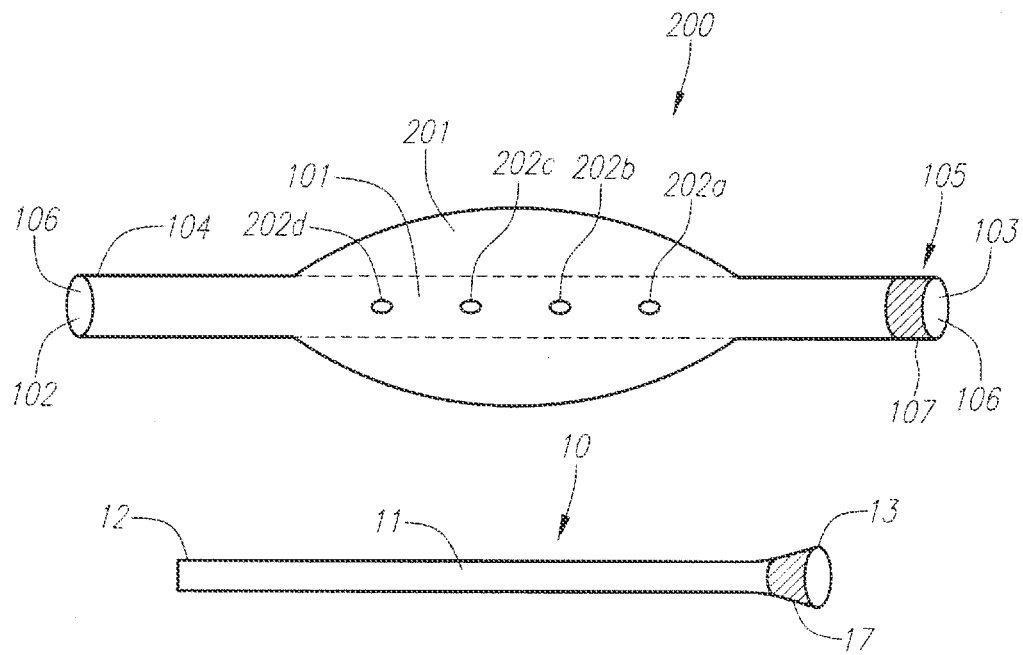
FIG. 2A illustrates an alternative embodiment of a nasal catheter having an expandable balloon mounted thereon for delivering a cooled liquid to the nasopharyngeal cavity and a grasping tool for pulling the catheter through the nasal cavity according to the present invention for non-invasive cerebral and systemic cooling.
Figure 6:
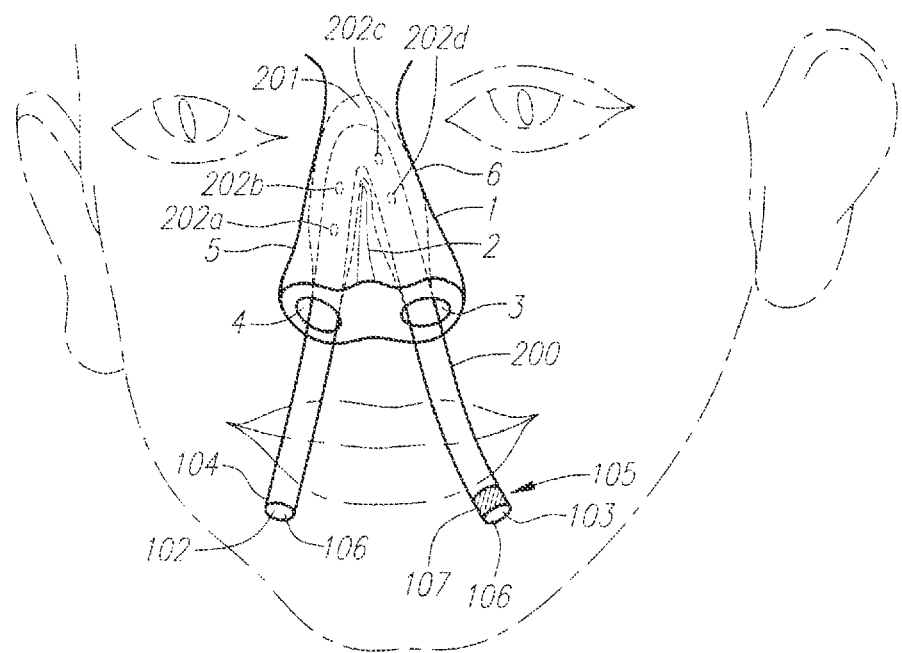
FIG. 6 illustrates an alternative embodiment of a nasal catheter having a flexible balloon mounted thereon positioned in a patient's nasal cavities for circulating a cold liquid in the nasopharyngeal cavity according to the present invention.

In an alternative embodiment, as shown in FIG. 2A, the nasal catheter 200 can have a flexible balloon 201 mounted circumferentially around the flexible tubular member 101 at an intermediate region between the proximal and distal ends 104, 105 of the flexible tubular member 101. The balloon 201 may be adhesively or thermally bonded to the flexible tubular member 101, or may otherwise be mounted on the flexible tubular member using techniques known in the arts. The flexible balloon is mounted on the nasal catheter 100 at a location such that in use the flexible balloon will be positioned in at least a portion of the patient's right and left nasal cavities. The flexible balloon 201 is preferably an elongate balloon having a length greater than twice the length of the patient's nasal cavity such that when the catheter is advanced through the patient's first nostril, around the nasal septum and out of the patient's second nostril, the flexible balloon 201 will be positioned around the nasal septum extending into the patient's right and left nasal cavities to a point in close proximity to the patient's first and second nostrils. For example, as shown in FIG. 6, the nasal catheter 200 may be positioned in a patient's nasal cavities 5,6 such that the flexible balloon 201 is located in the rear portions of the patient's right and left nasal cavities 5,6 and around the nasal septum 2. When a cold liquid is circulated through the lumen 106, the liquid flows through ports 202a-d to fill the flexible balloon 201 and the flexible balloon 201 expands to substantially fill a portion of the left and right nasal cavities 5,6 and the nasopharynx and touch the adjacent structures to provide increased contact with tissues in the nasal cavity and the roof of the pharynx, and an increased volume of cold liquid in the nasal cavities to thereby provide an increased cooling capacity. The flexible balloon 201 is preferably delivered to the patient's nasal cavities 5,6 in a collapsed state and then expanded to fill at least a portion of the left and right nasal cavities when the cold liquid is circulated therethrough.

As discussed above, the flexible balloons are preferably sized such that upon inflation, they are capable of making good contact with the surfaces of the nasal cavities, including the portion of the cavities that lies posterior to the cavernous sinus. In one embodiment, the length of the flexible balloon will depend upon the size of the nasal cavities and may be less than 20 cm long, alternatively less than 19 cm long, alternatively less than 18 cm long, alternatively less than 17 cm long, alternatively less than 16 cm long, alternatively less than 15 cm long, alternatively less than 14 cm long, alternatively less than 13 cm long, alternatively less than 12 cm long, alternatively less than 11 cm long. The flexible balloons may also have the shape of the nasal cavity. Alternatively, the flexible balloon may have a shape containing multiple fingers, or projections, such that, upon inflation, one or more fingers will have the opportunity to extend into and fill the meatus (superior, middle, and/or inferior) to maximize contact with the tissues in the nasal cavity. Alternatively, the flexible balloon may have multiple lobes to accomplish the same purpose of extending into and filling the meatus. The flexible balloons are also preferably oversized and made of a soft, conformable, elastomeric material to provide maximum surface contact with the nasal cavity. The assemblies may also include a check valve (not shown) that will release fluid, thereby reducing the pressure of the flexible balloons when they reach a certain pressure. Optionally, the flexible balloons may be made of a porous material that allows for the controlled release of drugs to the nasal cavity. Examples of materials for the elastomeric, flexible balloons include, but are not limited to, urethanes, vinyl (PVC), silicone. Examples of non-elastic materials include, but are not limited to, mylar, polyethylene, polypropylene, polystyrene, and polyvinylacetate.

A plurality of ports 202a-d are located along the outer wall of flexible tubular member 101. These ports 202a-d are spaced apart longitudinally and axially along the outer walls of catheter 10 and provide fluid communication between the flexible balloon 201 and lumen 106 such that the cold liquid can flow freely from lumen 106 into the balloon 201 and from the balloon 201 out to the lumen 106. For example, in some embodiments there may be about 2-20 ports distributed around the circumference of the flexible tubular member 101 and spaced apart to substantially cover the length of the balloon 201 on the flexible tubular member 101.

Figure 3A:
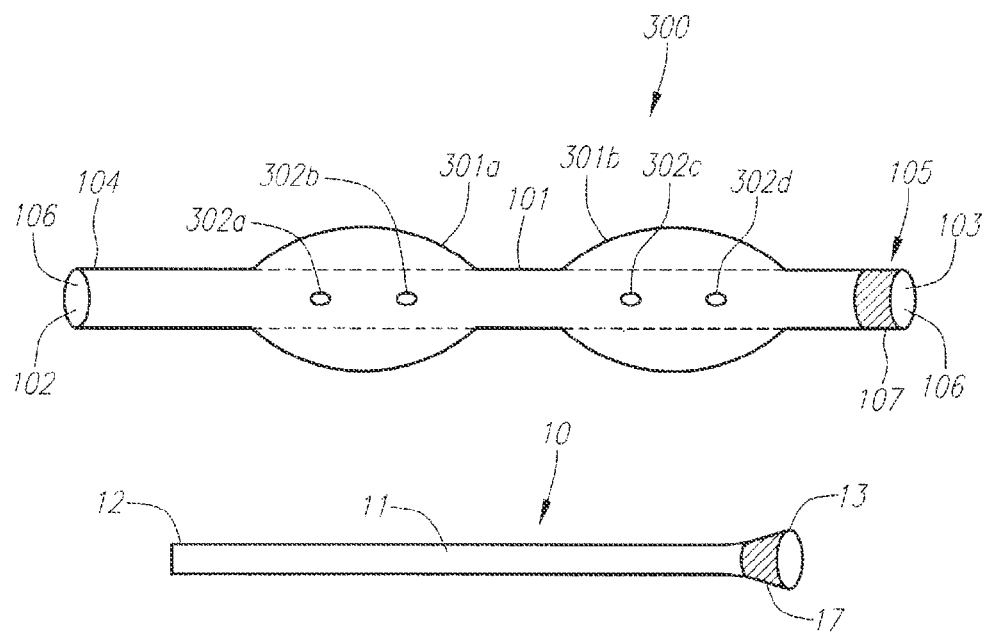
FIG. 3A illustrates an alternative embodiment of a nasal catheter having multiple balloons mounted thereon and a grasping tool for pulling the catheter through the nasal cavity according to the present invention for non-invasive cerebral and systemic cooling.
Figure 3B:
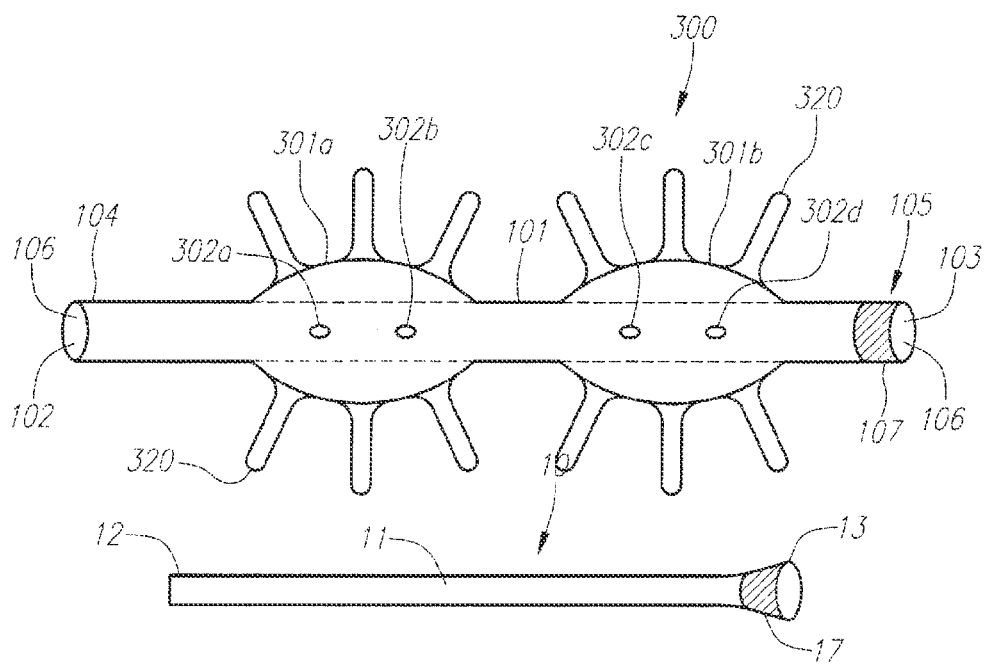
FIG. 3B illustrates an alternative embodiment of a nasal catheter having multiple balloons with one or more projections on the outer surface of the balloon, the balloon being mounted on the nasal catheter. A. gasping tool for pulling the catheter through the nasal cavity according to the present invention for non-invasive cerebral and systemic cooling is also depicted.

In an alternative embodiment, as shown in FIG. 3A and 3B, the nasal catheter 300 can have two flexible balloons 300, 301 mounted on the flexible tubular member 101 at an intermediate region between the proximal and distal ends 104, 105 of the flexible tubular member 101. The flexible balloons 301a,b are mounted on the nasal catheter 100 at a location such that in use flexible balloon 301a will be positioned in at least a portion of the patient's first nasal cavity and flexible balloon 301b will be positioned in at least a portion of the patient's second nasal cavities. The flexible balloons 301a,b preferably comprise elongate balloons having a length approximately the length of the patient's nasal cavity such that when the catheter is advanced through the patient's first nostril, around the nasal septum and out of the patient's second nostril, flexible balloon 301a will be positioned in the patient's first nasal cavity extending from the rear of the nasal cavity to point in close proximity to patient's first nostril and flexible balloon 301b will be positioned in the patient's second nasal cavity extending from the rear of the nasal cavity to point in close proximity to patient's second nostril. In use, the flexible balloons 301a,b can be delivered to the patient's nasal cavities in a collapsed state and then expanded to fill at least a portion of the left and right nasal cavities. As discussed above, the flexible balloons 301a,b are preferably sized such that upon inflation, they are capable of making good contact with the surfaces of the nasal cavities, including the portion of the cavities that lies posterior to the cavernous sinus. The length of the flexible balloons 301a,b will depend upon the size of the nasal cavities and may be less than 10 cm long, alternatively less than 9 cm long, alternatively less than 8 cm long, alternatively less than 7 cm long, alternatively less than 6 cm long, alternatively less than 5 cm long, alternatively less than 4 cm long, alternatively less than 3 cm long. As seen in FIG. 3B, in some embodiments, the flexible balloons 301a,b may have one or more fingers or projections 320 on the outer surface of the balloon to better conform to the inner walls of the patient's nasal cavities providing more direct surface contact for cooling the nasal cavities. Alternatively, the flexible balloons 301a,b can be sufficiently flexible to conform to the inner walls of the patient's nasal cavity when expanded.

In some embodiments, the chambers of the flexible balloons 301a,b may be filled with foam, e.g., open cell foam. The open-cell foam will aid in conforming the balloons 301a,b to the applicable cavity, for example, the nasal cavity, while also helping to distribute cooling. The foam may be made from urethane, latex, rubber, ethylene vinyl acetate (EVA), and other open-cell materials. In use, before insertion into the nasal cavity, the foam that is contained within the flexible balloon will be compacted using a vacuum source. After the compacted foam has been inserted into the nasal cavity, the vacuum will be released and the balloon will be allowed to expand to contact the surrounding tissue, Saline, water, PFC, refrigerant, anti-freeze solution, other cooling fluid, or a combination thereof can then be circulated through the catheter lumen 106 and into the flexible balloons 301a,b and open-cell foam to cool the surrounding tissue.

A plurality of ports 302a-d are located along the outer wall of flexible tubular member 101. These ports 302a-d are spaced apart longitudinally and axially along the outer walls of flexible tubular member 101 and provide fluid communication between the flexible balloons 301a,b and lumen 106 such that the cold liquid can flow freely from lumen 106 into the balloons 301a,b and from the balloons 301a,b out to the lumen 106. For example, in some embodiments there may be about 2-20 ports distributed around the circumference of the flexible tubular member 101 and spaced apart to substantially cover the length of the balloons 301a,b on the flexible tubular member.

As shown in FIGS. 1-3, a grasping tool 10 is provided for pulling the nasal catheters 100, 200, and 300 around the patient's septum and out of the patient's second nostril. The grasping tool 10 comprises an elongate member 11 having proximal and distal ends 12, 13. The elongate member 111 has a length sufficient for extending the distal end through a patient's second nostril to a point past the nasal septum while the proximal end remains outside of the patient's nostril such that the elongate member 11 can be used to engage the distal end of the nasal catheter at a point behind the nasal septum. The elongate member 11 may be made of a less flexible material than the nasal catheter 100 since it is not necessary for the elongate member to bend around the nasal septum. Preferably, the elongate member 11 is sufficiently rigid to be easily advanced through the patient's second nostril.

A magnet 17 is attached to the distal end 13 of the elongate member 11. The magnet 17 is preferably a rare earth magnet or electromagnet having sufficient magnetic power and strength to attract and couple with magnet 107 located on the distal end of the nasal catheter 100. In order to attract the magnet 107 on the nasal catheter, magnet 14 is selected to have the opposite polarity of magnet 107. The magnet 17 is also selected to have sufficient magnetic force to maintain the coupling with magnet 107 in use when the elongate member 11 is withdrawn from the patient's second nostril to pull the nasal catheter through the second nostril. The magnet 17 may be integral to the distal end 13 of the elongate member 11. Alternatively, the magnet 17 may be secured to the distal end of the elongate member 11 using an adhesive, tape or any suitable method know in the art. For examples of alternative magnetic catheters and methods used to secure a nasal tube see U.S. Pat. No. 6,837,237, issued on Jan. 4, 2005, and U.S. Pat. No. 6,631,715, issued on Oct. 14, 2003, both of which are hereby incorporated by reference in their entirety.

The nasal catheters of the present invention can also be used in combination with other cooling or heating devices. For example, the catheter may be used in combination with a helmet or cooling cap for synergistic cooling as seen in, for example, U.S. Pat. No. 6,962,600, which is hereby expressly incorporated by reference in its entirety. Additionally, the nasal catheters may be used in combination with a warming blanket to enhance the gradient between the cerebral temperature and the systemic temperature where systemic cooling is inadequate to bring down the brain temperature. In one embodiment, a heat pump could be used in conjunction with a cooling helmet or cap and a warming blanket. The beat pump could take heat from the liquid being circulated to the cooling helmet or cap and pump the heat into the warming blanket. The heat pump could use a refrigerant or thermoelectric cycle.

Figure 5A:
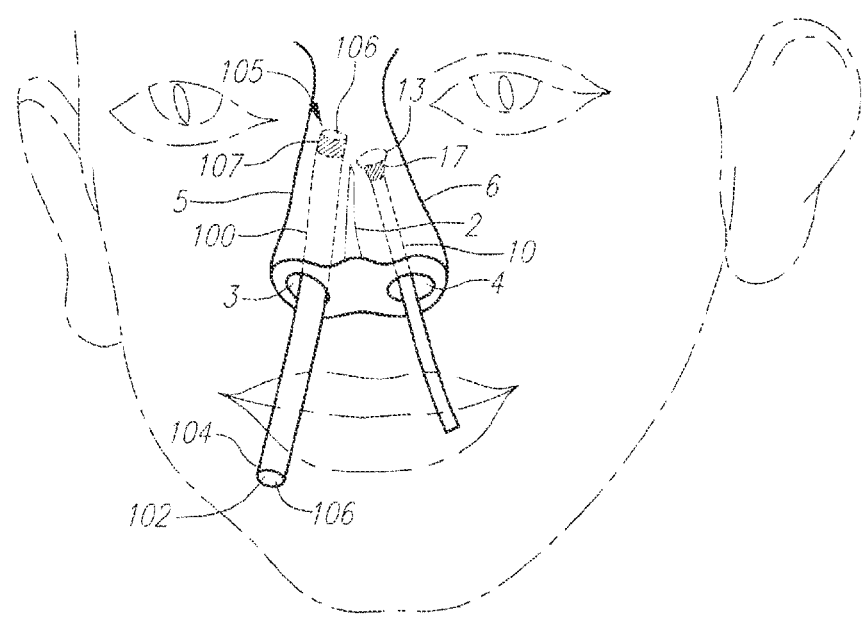
FIG. 5A illustrates the nasal catheter of FIG. 1 placed in a patient's first nostril and the grasping tool placed in the patient's second nostril according to the present invention.

In use, as shown in FIG. 5A, the nasal catheter 100 is inserted into a patient's right nostril 3 and advanced through the right nasal cavity 5 until the distal end 105 of the nasal catheter 100 is positioned at a point behind the nasal septum 2. The proximal end 103 of the nasal catheter 100 extends out of the patient's right nostril 3. The grasping tool 10 is similarly inserted in to the patient's left nostril 4 and advanced through the left nasal cavity 6 until the distal end of the grasping tool 10 is positioned at a point behind the nasal septum 2. In some embodiments, a lubricant and/or a nasal anesthetic may be applied to the outer surface of the nasal catheter 100 and the grasping tool 10 for ease of insertion and patient comfort.

Figure 5B:
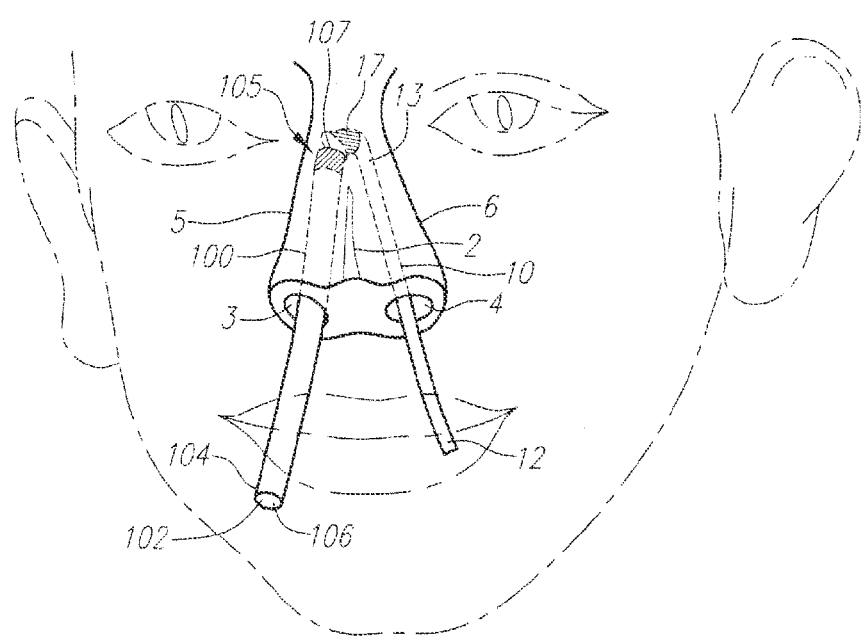
FIG. 5B illustrates the nasal catheter and the grasping tool of FIG. 5A connected behind the patient's septum according to the present invention.

As shown in FIG. 5B, once both the nasal catheter 100 and the grasping tool 10 have been advanced through the patient's nasal cavities beyond the nasal septum 2, the proximal end 12 of the grasping tool 10 may be manipulated to engage the distal end 13 of the grasping tool 11 with the distal end 105 of the nasal catheter 100. For example, as shown here, the magnet 17 on the distal end 13 of the grasping tool 10 engages and magnetically couples with the magnet 107 on the distal end 105 of the nasal catheter 100. The magnets 17 and 107 have opposite polarity such that when the magnet 17 is placed in close proximity to magnet 107, magnet 17 will attract and engage magnet 17 thereby connecting the distal ends 13,105 of the nasal catheter and the grasping tool. In alternative embodiments, the distal end of the grasping tool may comprise a hook, clasp or clip for connecting to the distal end of the nasal catheter.

Figure 5C:
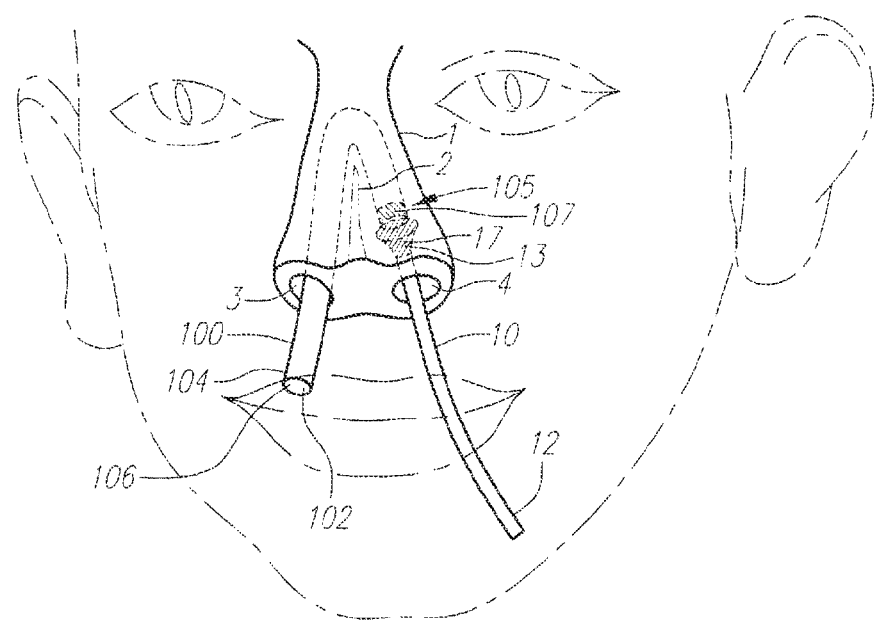
FIG. 5C illustrates the grasping tool of FIG. 5B being withdrawn from the patient's second nostril to pull the tip of the nasal catheter around the septum and out through the patient's second nostril according to the present invention.

As shown in FIG. 5C, the grasping tool 10 is then pulled back through the patient's left nasal cavity 6 and withdrawn from the patient's left nostril 3. The magnetic coupling between the distal end 105 of the nasal catheter 100 and the distal end 15 of the grasping tool 10 is sufficiently strong that the connection will not uncouple when the grasping tool is pulled back through the patient's left nasal cavity 6. Thus, the distal end 105 of the nasal catheter 100 is pulled around the nasal septum 2 and through the patient's left nasal cavity 6. The grasping tool 10 is preferably withdrawn until the distal end 105 of the nasal catheter 100 has been pulled completely through the patient's left nasal cavity 6 and out of the patient's left nostril 3. Once the distal end of the nasal catheter 100 has been pulled though the left nostril 3, the nasal catheter 100 and the grasping tool 10 may be separated. The nasal catheter 100 is now looped though the patient's first nostril 4, around the nasal septum 2 and out of the patient's second nostril 3, as shown in FIGS. 4A and 4B, such that a cold fluid can be flowed through the patient's nasal cavities 5,6. The proximal and distal ends 104, 105 of the nasal catheter 100 can be manipulated as necessary to place the expandable region or the flexible balloon(s) of the nasal catheter in the correct position within the patient's nasal cavities 5,6.

Figure 5D:
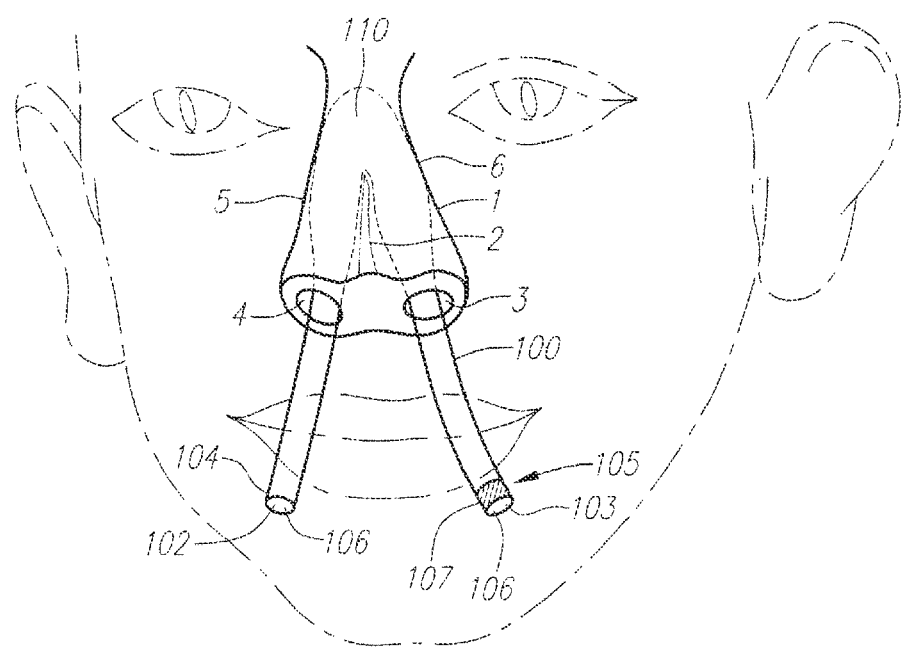
FIG. 5D illustrates the nasal catheter of FIG. 5A positioned in the patient's first and second nasal cavities and around the patient's nasal septum with a cold Liquid being circulated through the expandable region of the nasal catheter.

The proximal end 104 of the nasal catheter is placed in fluid communication with a liquid source, such as a fluid reservoir 145, and a cold liquid, such as water, a refrigerant, saline, PFC, anti-freeze solution, a combination thereof or any other suitable cold liquid, is circulated through the lumen 106 of the nasal catheter 100 and out the distal end 105 of the nasal catheter 100 for cooling the patient's nasal cavities 5,6. As shown in FIG. 5D, the expandable region 110 of the nasal catheter 100 expands to place the expandable region 110 containing the cold liquid in contact with the adjacent anatomy of the nasal cavities 5,6 to provide for cooling of the brain by convection or heat exchange from the cold liquid in the expandable region 110 of the nasal catheter 100 to the warm nasal cavities 5,6 and the roof of the pharynx. In some embodiments, a refrigerated pump (not shown) can be connected to the proximal end 104 of the nasal catheter 100 to circulate the cold fluid through the lumen 106 at a specific flow rate. The used liquid may be allowed to flow freely out of the distal end 105 of the nasal catheter 100. Alternatively, as seen in FIG. 4B, the distal end 105 of the nasal catheter 100 can be connected to the refrigerated pump 147 to continuously cool and re-circulate the liquid through the nasal catheter 100.

The cooling fluid used with these inventions may include, but is not limited to, water, saline, PFC, anti-freeze solution, or a combination thereof. The temperature of the cooling fluid will preferably be below body temperature. The temperature of the cooling fluid may be between about 37° C. to about −20° C., alternatively between about 30° C. to about −20° C., alternatively between about 20° C. to about −20° C., alternatively about 0° C., alternatively about 5° C., alternatively about −5° C., alternatively between about −5° C. to about 10° C., alternatively between about −5° C. to about 5° C., alternatively between about 0° C. to about 5° C. When saline is used as the cooling fluid, the saline will preferably be about 0° C.

The liquid flow rate is also a critical factor for cerebral cooling. The cooling fluid should re-circulate at a fast enough rate to maintain the low temperatures within the balloon or expandable region. The flow rate of the cooling liquid may be between about 5 mL and about 5 L/min, alternatively between about 100 and about 400 ml/min, alternatively between about 200 and about 300 ml/min, alternatively between about 150 to about 200 ml/min. In some embodiments, the liquid may be circulated at a faster rate initially to induce rapid cerebral cooling in order to create a gradient between the cerebral and systemic temperatures. The gradient between the cerebral and systemic cooling that forms over time is desirable in order to minimize damage to other organs and hypothermia during the cerebral cooling. For example, the liquid may be initially circulated at a rate to induce cerebral cooling at a rate of at least about 0.1° C. in hour, alternatively at least about 1° C. in hour, alternatively at least about 1.5° C. in hour, alternatively at least about 2° C. in hour, alternatively at least about 3° C. in hour, alternatively at least about 4° C. in hour, alternatively at least about 5° C. in hour between the cerebral temperature and the systemic temperature. This sudden initial exposure to cold induces a vasoconstriction response in the carotid arteries causing the carotid arteries to constrict, which helps isolate the cerebral vasculature and prevent warmer blood from the heart traveling to the brain and the cooler blood in the brain from traveling to and thereby cooling the rest of the body. This initial vasoconstriction response thus further aids the cooling process by preventing warmer blood from traveling to the head. In addition, the initial cooling lowers the metabolic demand of the head, thus the carotid artery can further constrict and further isolate the head.

After the initial induction, in order to maintain sufficient cooling, the cold liquid may be circulated through the nasal catheter at a lower flow rate. The lower flow rate may result in a gradient between the cerebral and systemic temperature of at least about 0.1° C., alternatively at least about 0.2° C., alternatively at least about 0.3° C., alternatively at least about 0.4° C., alternatively at least about 0.5° C., alternatively at least about 0.6° C., alternatively at least about 1.0° C., alternatively at least about 1.5° C., alternatively at least about 2.0° C., alternatively at least about 2.5° C., alternatively at least about 3.0° C., alternatively at least about 3.5° C., alternatively at least about 4.0° C., alternatively at least about 4.5° C., alternatively at least about 5.0° C. The administration of the liquid may be continued until the cerebral temperature is reduced to 35° C. or below, more preferably to 34° C. or below, more preferably to 33° C. or below. In certain methods, the administration of the liquid may be continued to provide for systemic cooling as well as cerebral cooling.

The patient's cerebral, systemic, and nasal temperatures may also be monitored during this procedure. Here, the cold liquid may be delivered at a flow rate sufficient to achieve a gradient of not greater than about 0.5° C. between the outer surface of the brain and the inner core of the brain. The cold liquid may also be delivered at a flow rate sufficient to achieve a gradient of at least about 1.0° C. between the cerebral temperature and the systemic temperature. The cold liquid may also be delivered at a flow rate sufficient to achieve cerebral cooling at a rate greater than about 1.0° C. in hour. The cold liquid may also be delivered at a flow rate sufficient to achieve a temperature in the nasal cavity of about 4.0° C. or less.

In some embodiments, as shown in FIG. 6, the nasal catheter 200 has a flexible balloon 201 mounted circumferentially around the flexible tubular member 101 at an intermediate region between the proximal and distal ends 104, 105 of the flexible tubular member 101. The nasal catheter 200 may be positioned in a patient's nasal cavities 5,6 using the method described above, such that the flexible balloon 201 is located in the rear portions of the patient's right and left nasal cavities 5,6 and around the nasal septum 2. When the proximal end 104 of the nasal catheter 200 is placed in fluid communication with a liquid source, a cold liquid, such as water, a refrigerant, saline, PFC, anti-freeze solution, a combination thereof or any other suitable cold liquid, is circulated through the lumen 106 of the nasal catheter 200 and the ports 202a-d, the flexible balloon 201 expands to place the surface of the balloon 201 in contact with the walls of the nasal cavities 5,6 and the roof of the pharynx to provide for cooling of the brain by convection or heat exchange from the cold liquid in the flexible balloon to the warm nasal cavities 5,6 and pharynx. The liquid can be continuously re-circulated through the balloon 201 using a pump or other means. In order to optimize cooling and minimize tissue damage, it may be desirable to continuously inflate and deflate flexible balloon.

Figure 2B:
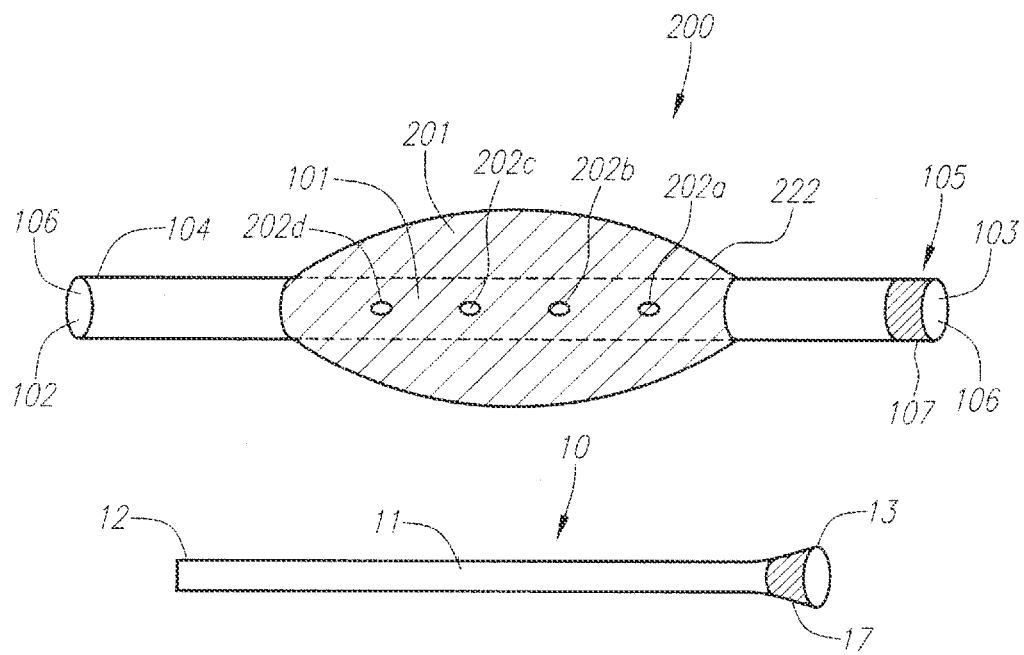
FIG. 2B illustrates an alternative embodiment of a nasal catheter having an expandable balloon with a gel, the expandable balloon mounted on the catheter for delivering a cooled liquid to the nasopharyngeal cavity. A grasping tool for pulling the catheter through the nasal cavity according to the present invention for non-invasive cerebral and systemic cooling is also depicted.

Optionally, as seen in FIG. 2B, a gel 222 may also be applied to the exterior of flexible balloon 201 before insertion into the nasal cavities 5,6. The gel would preferably have good thermal conduction properties and be a better conductor than air. Additionally, the gel could also act as a lubricant to assist in the insertion. The gel may include, but is not limited to, any aqueous gel, a poloxamer-based gel, a cellulose gel (such as KY jelly), a nasal-packing jelly, or a thermal gel.

In use, the pressure in these flexible balloons for use in the nasal cavity can oscillate between lower and higher pressures. In other words, the fluid can be infused to fill the chamber defined by the balloon either slowly or quickly. When expanded at higher pressures, presumably more heat transfer will occur due to increased contact with the nasal cavity. Extended periods at higher pressures, however, may not be desirable due to possible problems with stopping blood flow in the surrounding tissue. Additionally, the act of pulsing the liquid would result in increased circulation of the liquid. Rapid pulsing, for the purposes of mixing the liquid within the balloon chamber, could range from about 0.5 to about 200 Hz, alternatively from about 1 to about 150 Hz, alternatively from about 1 to about 100 Hz, alternatively from about 10 to about 100 Hz, alternatively from about 25 to about 100 Hz. Slower pulsing could be used to effect physiologic responses, such as deflating the balloon to allow blood flow to resume circulation in the cooled area. Slower pulsing could range from about one inflation per second to about one inflation per 10 minutes, alternatively from about one inflation per second to about one inflation per 5 minutes, alternatively from about one inflation per second to about one inflation per 3 minutes. Alternatively, the balloon could be inflated approximately once every 30 seconds, alternatively once every 1 minute, alternatively once every 2 minutes, alternatively once every 3 minutes, alternatively once every 4 minutes, alternatively once every 5 minutes, alternatively once every 6 minutes, alternatively once every 7 minutes, alternatively once every 8 minutes, alternatively once every 9 minutes, alternatively once every 10 minutes. During these slower cycling periods, the balloon could remain inflated for approximately 1% of the cycling period, alternatively approximately 5% of the cycling period, alternatively approximately 10% of the cycling period, alternatively approximately 20% of the cycling period, alternatively approximately 30% of the cycling period, alternatively approximately 40% of the cycling period, alternatively approximately 50% of the cycling period.

Cooling Calculations

The following calculations estimate the maximum cooling that can be obtained when a chilled liquid is circulated through the nasal cavity, where the chilled fluid is either directly in contact with the nasal tissues or contained in a flexible membrane 'balloon' within the nose.

A cooling liquid is circulated into and out of the nasal cavity. The following calculations are done assuming that the chilled fluid will be an aqueous fluid. The following are properties of water:

Density: 1 gram/ml
Heat capacity: 1 cal/gram-° C.

The liquid will enter the nasal cavity at a temperature well below body temperature, and exit at a warmer temperature. The warming of the water will be equal to the cooling of the body, so the calculations for heat added to the water is the same as that for heat removed from the body.

$$Q'=c*m*(T2-T1) \text{ or } Q'=cm\Delta T \quad \text{Equation 1}$$

$Q'$=the rate of heat transfer
m=the mass flow rate of the liquid administered
C=the heat capacity of the liquid
$T1$=the temperature of the liquid at administration
$T2$=the temperature to which the liquid is warmed If the flow rate is 500 ml/min, inlet temperature is 2° C., outlet temperature is 4° C.

Heat Transfer=500ml/min*1g/ml*1cal/gm° C.*(4° C.−2° C.)=1000cal/min

Conversion factors: 1 calorie/minute=0.069 78 watt
1000 cal/min*0.06978 Watt/cal/min=70 Watts The cooling of the whole body can be calculated using the same equation as above. The heat capacity of the human body is generally accepted to be 0.85 cal/gm ° C. For this calculation, other sources of heat entering or leaving the body, and heat generated in the body are neglected, as it is likely those aspects balance out in a stable patient. Cooling therefore reduces to the equation below.

Whole body cooling($\Delta T$)=Heat removed/(mass*heat capacity)

Continuing the example above, for a 75 kg patient, the temperature change is calculated below to be 0.93° C. per hour, which is close to the target cooling rate for patients.

$$\text{Temperature change} = 1000 \text{ cal/min}/(75{,}000 \text{ grams} * 0.85 \text{ cal/gram} °C.$$
$$= 0.0157 \text{ °C./min}$$
$$= 0.93 \text{ °C. per hour}$$

For whole body cooling (WBC), the following formula can be developed from the above:

WBC(° C./hr)=$\Delta T$(liquid,° C.)*Flow rate(ml/mm)/(Patient wt(kg)*14.3)

or

WBC(° C./hr)=Cooling(watts)/Patient Weight(kg)

The surface of the balloon may be treated or modified to maximize thermal conductance. A gel may also be optionally applied to the exterior of flexible balloons 204, 254 before insertion into the nasal cavity. The gel would preferably have good thermal conduction properties and be a better conductor than air. Additionally, the gel could also act as a lubricant to assist in the insertion. The gel would help the flexible balloon make better contact with the mucous membrane and would also fill some of the air space in the nasal cavity, which should increase effective surface area. The gel may include, but is not limited to, any aqueous gel, a poloxamer-based gel, a cellulose gel (such as KY jelly), a nasal-packing jelly, a hydrogel (such as MeroGel or GelFilm), or a thermal gel. Alternatively, sponges may be attached to the surface of the balloon. Sponges, such as PVA sponges, are commonly used as packing material in noses and will conform to the shapes of the nasal cavity when wet. Alternatively, a hydrophilic coating may also be applied to the outer surface of the balloon to prevent beading on the outside.

Advantages of this apparatus and method include rapid circulation of the cooling fluid, rapid transfer of heat from the flexible balloon to the membranes of the nasal cavity, and flexibility in choice of coolant because the fluid is contained. Heat is transferred through the mucosa from the pool of blood in the cavernous sinus to the cooling fluid in the flexible balloon, thereby cooling the pool of blood in the cavernous sinus. Consequently, the blood in the carotid arteries, which runs through the cavernous sinus, is also cooled as it travels to the brain. In particular, the maximal heat exchange will likely be with the ascending carotid arteries immediately before entry into the intracranial space and the terminal portion of the extracranial internal carotid artery.

Although the foregoing invention has, for the purposes of clarity and understanding, been described in some detail by way of illustration and example, it will be obvious that certain changes and modifications may be practiced which will still fall within the scope of the appended claims.

What is claimed is:

1. A method for cerebral cooling, comprising the steps of:
    introducing a catheter through a first nostril of a patient, the catheter having a proximal end, a distal end, a single lumen therebetween, the lumen having openings at the proximal and distal ends of the catheter, the catheter having an expandable region intermediate between the proximal and distal ends;
    advancing the distal end of the catheter through the nasal cavity, around the nasal septum and out a second nostril of the patient so that the expandable region lies within at least a portion of the patient's first and second nasal cavities; and
    circulating a cold fluid into the proximal opening of the lumen, through the lumen at the proximal end of the catheter, through the expandable region, through the lumen at the distal end of the catheter, and out of the distal opening of the lumen to cool the nasal cavities.

2. The method of claim 1, wherein the step of advancing the distal end of the catheter through the nasal cavities and out a second nostril of the patient is performed by the steps of advancing a grasping tool into the second nostril beyond the nasal septum, grasping the distal end of the catheter, and pulling the distal end of the catheter out the second nostril.

3. The method of claim 2, wherein the grasping tool comprises a hook.

4. The method of claim 2, wherein the grasping tool comprises a clasp.

5. The method of claim 2, wherein the grasping tool comprises a clip.

6. The method of claim 1, wherein the step of advancing the distal end of the catheter through the nasal cavities, around the nasal septum and out a second nostril of the patient is performed by the steps of:
    advancing the distal end of the catheter through the first nostril to a point beyond the nasal septum;
    advancing a grasping tool having a first magnet attached at a distal end into the second nostril;
    engaging the first magnet with a second magnet attached to the distal end of the catheter to magnetically couple the distal end of the catheter and the distal end of the grasping tool; and
    pulling the distal end of the catheter around the nasal septum and out the second nostril.

7. The method of claim 1, wherein the expandable region comprises one or more flexible balloons mounted at a location intermediate between the proximal and distal ends of the catheter and one or more ports spaced apart along the expandable region, said ports providing fluid communication between the catheter lumen and the one or more flexible balloons.

8. The method of claim 7, wherein the step of circulating a cold fluid further comprises expanding the one or more flexible balloons to substantially fill a portion of the nasal cavities.

9. The method of claim 7, wherein the one or more flexible balloons have one or more projections on the outer surface.

10. The method of claim 7, wherein the expandable region comprises two flexible balloons mounted at a location intermediate between the proximal and distal ends of the catheter.

11. The method of claim 7, further comprising a conductive gel applied to an exterior of the one or more flexible balloons.

12. The method of claim 7, further comprising eluting a drug from an exterior of the one or more flexible balloons.

13. The method of claim 1, wherein the cold fluid is selected from a group consisting of water, saline, PFC, antifreeze solution and a combination thereof.

14. The method of claim 1, further comprising a reservoir containing the cold fluid, the reservoir in fluid communication with the lumen at the proximal end of the catheter.

15. The method of claim 1, wherein the cold fluid is continuously circulated through the catheter using a pump.

16. The method of claim 1, wherein the cold fluid is infused through the catheter at a flow rate of between about 5 ml/min and about 5 L/min.

17. The method of claim 1, wherein the cold fluid is infused through the catheter at a flow rate of between about 100 ml/min and about 1 L/min.

18. The method of claim 1, wherein the cold fluid is infused through the catheter at a flow rate of between about 200 ml/min and about 600 ml/min.

19. A device for cerebral cooling, comprising:
    a catheter having a proximal end, a distal end, a single lumen therebetween, the lumen having openings at the proximal and distal ends of the catheter, the catheter adapted for advancing the distal end through a first nostril of a patient, through a first and second nasal cavity, around a nasal septum and out a second nostril of the patient;
    a first magnet located at the distal end of the catheter;
    a first balloon mounted on the catheter at a location intermediate between the proximal and distal ends, the first balloon adapted to lie within the nasal cavities and expand to fill at least a portion of the patient's first and second nasal cavities when a cold fluid is circulated through the opening in the lumen at the proximal end of the catheter, through the first balloon, and through aperture in the lumen at the distal end of the catheter to cool the nasal cavity;
    an elongate member having a proximal end, a distal end, and a second magnet located on the distal end, the elongate member adapted for advancing the distal end through a second nostril of the patient, the second magnet configured for engaging the first magnet to magnetically couple the distal end of the catheter and the distal end of the elongate member.

20. The device of claim 19, further comprising a second balloon mounted in a location intermediate between the proximal and distal ends of the catheter, the second balloon adapted to expand to fill at least apportion of the patient's nasal cavities when a cold fluid is circulated therethrough, wherein the first balloon is adapted to lie substantially within the patient's first nasal cavity and the second balloon is adapted to lie substantially within the patient's second nasal cavity.

21. The device of claim 20, further comprising one or more ports spaced along the catheter, the one or more ports configured to provide fluid communication between the first and second balloons and the lumen of the catheter.

* * * * *